(12) United States Patent
Chennell et al.

(10) Patent No.: US 6,484,583 B1
(45) Date of Patent: Nov. 26, 2002

(54) THROUGH-TRANSMISSION ULTRASONIC INSPECTION APPARATUS AND METHOD

(75) Inventors: Richard Scott Chennell, Liberty Township, OH (US); Jon Russel Dierdorf, Okeana, OH (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/670,190

(22) Filed: Sep. 26, 2000

(51) Int. Cl.⁷ ............................................. G01N 9/24
(52) U.S. Cl. ............................. 73/623; 73/660; 73/666
(58) Field of Search ......................... 73/600, 602, 583, 73/799, 639, 641, 643, 660, 666, 623, 628

(56) References Cited

U.S. PATENT DOCUMENTS

| | | | | |
|---|---|---|---|---|
| 4,194,400 A | * | 3/1980 | Staff | 73/623 |
| 4,217,782 A | * | 8/1980 | Pont | 73/637 |
| 4,519,251 A | * | 5/1985 | Dickson | 73/639 |
| 4,718,277 A | * | 1/1988 | Glascock | 73/622 |
| 4,787,247 A | * | 11/1988 | Wuchinich et al. | 73/620 |
| 5,203,869 A | * | 4/1993 | Bashyam | 73/640 |
| 5,237,874 A | * | 8/1993 | Latimer et al. | 73/621 |
| 5,781,007 A | * | 7/1998 | Partika et al. | 324/220 |
| 6,311,538 B1 | * | 11/2001 | Martin | 73/1.04 |

* cited by examiner

Primary Examiner—Hezron Williams
Assistant Examiner—Jacques M. Saint-Surin
(74) Attorney, Agent, or Firm—V. G. Ramaswamy; Gregory O. Garmong

(57) ABSTRACT

A hollow composite structure is inspected using an ultrasonic inspection apparatus including a yoke having a base, a first arm extending from the base, and a second arm extending from the base parallel to the first arm. A first ultrasonic transducer is affixed to the first arm, and a second ultrasonic transducer is affixed by a spring mount to the second arm in facing relation to the first ultrasonic transducer. A retractor is affixed to the spring mount to permit the second ultrasonic transducer to be retracted away from the first ultrasonic transducer against a spring bias. The ultrasonic inspection apparatus is positioned by placing one of the arms adjacent to the interior surface, one of the arms adjacent to the exterior surface, and the base extending through the access opening. The retractor is operated to retract the second ultrasonic transducer so that the two ultrasonic transducers may be moved laterally across the interior surface and the exterior surface, and released so that the two ultrasonic transducers are in a facing relation to each other with the piece of composite material captured therebetween. The ultrasonic transducers are operated to achieve through-transmission testing of the wall of the hollow structure.

15 Claims, 3 Drawing Sheets

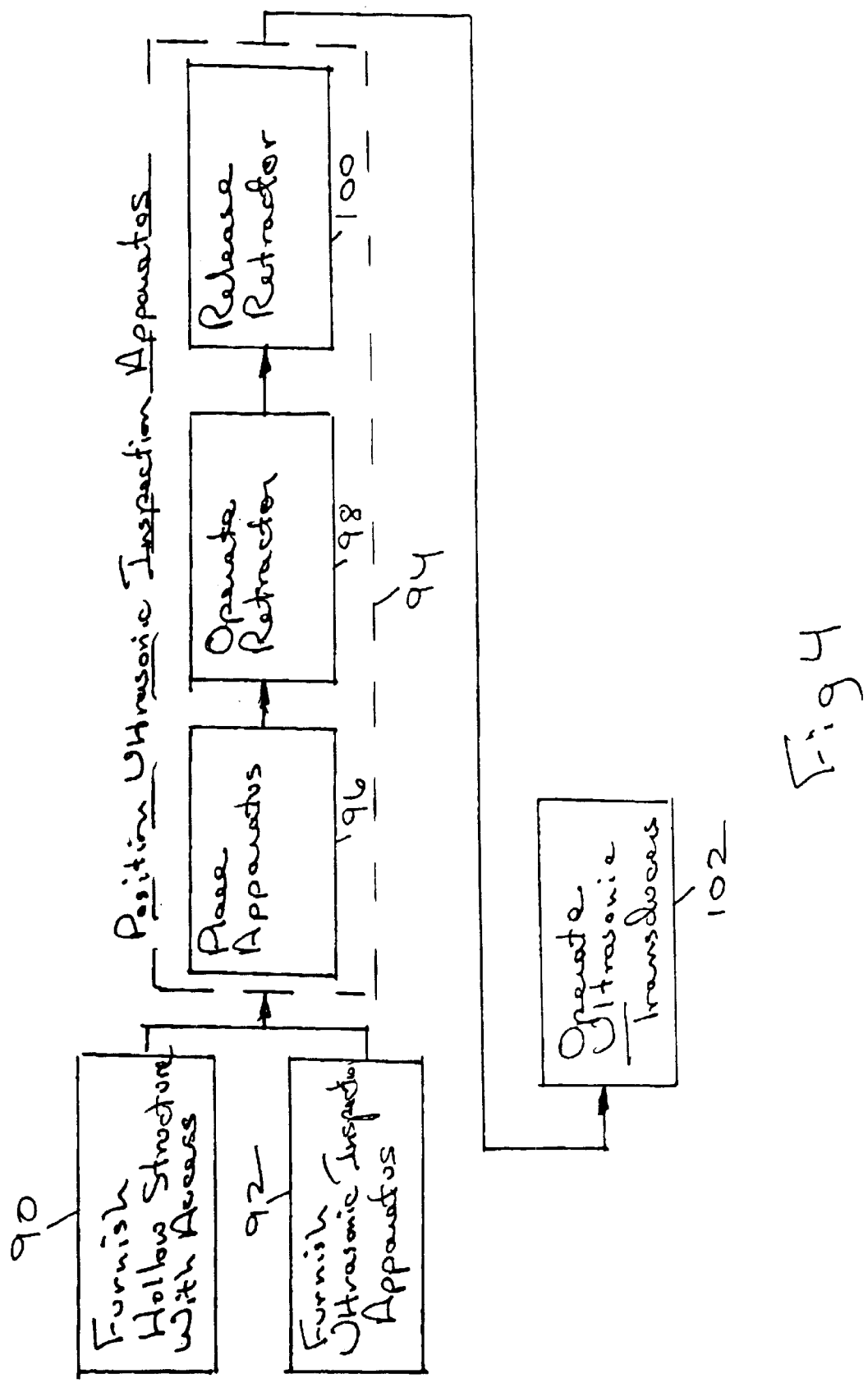

THROUGH-TRANSMISSION ULTRASONIC INSPECTION APPARATUS AND METHOD

The invention herein described was made in the course of or under a contract or subcontract thereunder (or grant) with the Department of the Navy.

FIELD OF THE INVENTION

This invention relates to ultrasonic inspection apparatus, and, more particularly, to an ultrasonic inspection apparatus useful to perform through-thickness ultrasonic measurements of difficult-to-access articles.

BACKGROUND OF THE INVENTION

Ultrasonic inspection is widely used to detect flaws in materials and structures. One type of flaw is delaminations between two of the multiple plies of composite material that are collated and then bonded together to form a composite structure. The delaminations may occur either during initial processing and fabrication, or during service. Such composite structures are widely used in aerospace and other applications, and there is a continuing concern with delaminations and other types of flaws.

In one type of ultrasonic inspection, termed through-thickness inspection, ultrasonic transducers are positioned in a facing relationship but contacting the opposite sides of a piece of the composite material that forms the composite structure. An ultrasonic signal is transmitted by one of the transducers, propagated through the piece of composite material, and received by the other transducer. The signal is analyzed by associated electronics. The presence and extent of flaws such as porosity and delaminations between the plies of the composite material sampled between the ultrasonic transducers may be assessed from the signal. For the analysis of many types of flaws in composite materials, only through-thickness ultrasonic measurements produce the required information. Reflection measurements wherein a single transducer is used are not operable to yield the required results.

Although this ultrasonic inspection approach is straightforward in principle, it is complicated by the fact that it is sometimes difficult to precisely position the ultrasonic transducers in a facing relation due to the confined spaces that are encountered in practice or because of the relative inaccessibility of one side of the composite article.

As an example, delamination flaws are sometimes found adjacent to access ports in hollow composite structures such as the outer bypass duct of a gas turbine aircraft engine. The flaws may be detected by disassembling the bypass duct structure from the engine and testing it using bench-type ultrasonic inspection apparatus in a testing laboratory. This testing is expensive and time consuming, and is not practical for many situations such as field inspections. As a result, the structure is not tested as thoroughly or as often as might otherwise be desired to check for the presence of flaws.

There is a need for an improved approach to the inspection of such composite structures, which is effective but easy and quick to perform. The present invention fulfills this need, and further provides related advantages.

BRIEF SUMMARY OF THE INVENTION

The present invention provides an ultrasonic inspection apparatus and method for its use in through-thickness ultrasonic measurements of workpieces. The approach is particularly well suited for use in performing ultrasonic through-thickness measurements of difficult-to-access workpieces such as the walls of hollow structures. The approach achieves automatic alignment of the transmitting and receiving transducers. It avoids the need to disassemble the structure to otherwise permit access to both sides of the wall. The approach allows the determination of degradation of the integrity of the structure over time, so that the lifetime prior to repair or replacement may be estimated. The apparatus permits inspection around the entire periphery of an access opening, over a range of distances from the opening. The apparatus is relatively light in weight, so that it is hand held and may be positioned and operated by a single person.

An ultrasonic inspection apparatus comprises a yoke having a base, a first arm extending from the base, and a second arm extending from the base parallel to the first arm. There is a first ultrasonic transducer affixed to the first arm, a second ultrasonic transducer in facing relation to the first ultrasonic transducer, and a spring mount attaching the second ultrasonic transducer to the second arm. The spring mount comprises a spring biasing the second ultrasonic transducer toward the first ultrasonic transducer with a spring bias. A retractor, preferably a manual retractor, is affixed to the spring mount so as to permit the second ultrasonic transducer to be retracted away from the first ultrasonic transducer against the spring bias. In use of the apparatus an electronics system is in electrical communication with the first ultrasonic transducer and the second ultrasonic transducer. The electronics system transmits a driver signal to one of the ultrasonic transducers and receives a received signal from the other of the ultrasonic transducers.

A method for determining the presence of flaws in a composite material in a hollow structure comprises the step of furnishing a hollow structure having a wall comprising a piece of composite material. The wall has an interior surface, an exterior surface, and an access opening therethrough extending between the interior surface and the exterior surface. The hollow structure preferably comprises a component of an aircraft, more preferably a component of a gas turbine engine, and most preferably an outer bypass duct of a gas turbine engine. In the latter case, the access is an access port in the outer bypass duct. An ultrasonic inspection apparatus of the type described above is furnished. The ultrasonic inspection apparatus is positioned by the steps of placing one of the arms adjacent to the interior surface, one of the arms adjacent to the exterior surface, and the base extending through the access opening. The retractor is operated to retract the second ultrasonic transducer so that the two ultrasonic transducers may be moved laterally across the interior surface and the exterior surface, and then released so that the two ultrasonic transducers are in a facing relation to each other with the piece of composite material captured therebetween. Optionally, a coupling medium, such as water, a jell, or oil, may be placed onto the composite material or onto the faces of the transducers, to aid in coupling the ultrasonic signal between the transducer and the composite material. The ultrasonic transducers are operated to send an ultrasonic signal from one of the ultrasonic transducers to the other of the ultrasonic transducers.

The present approach provides a convenient approach to positioning two ultrasonic transducers in precise alignment on the opposite faces of a workpiece which is otherwise difficult to access, with a lightweight, hand-held apparatus. The regions of a composite workpiece around the periphery of an access opening are particularly susceptible to delamination failures between the plies of composite material that are laminated together to form the composite structure, as well as other types of flaws. The apparatus allows the transducers to be quickly and accurately positioned near the access opening, so that ultrasonic measurements may be readily made without any disassembly. This capability not only reduces inspection time and cost, but also increases the frequency at which inspections may be made, an important safety consideration. Inspections conducted over a period of time allow the useful lifetime of the part to be estimated.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIG. 4 is a block flow diagram of an approach for practicing the invention.

DETAILED DESCRIPTION OF THE INVENTION

Figure 1:
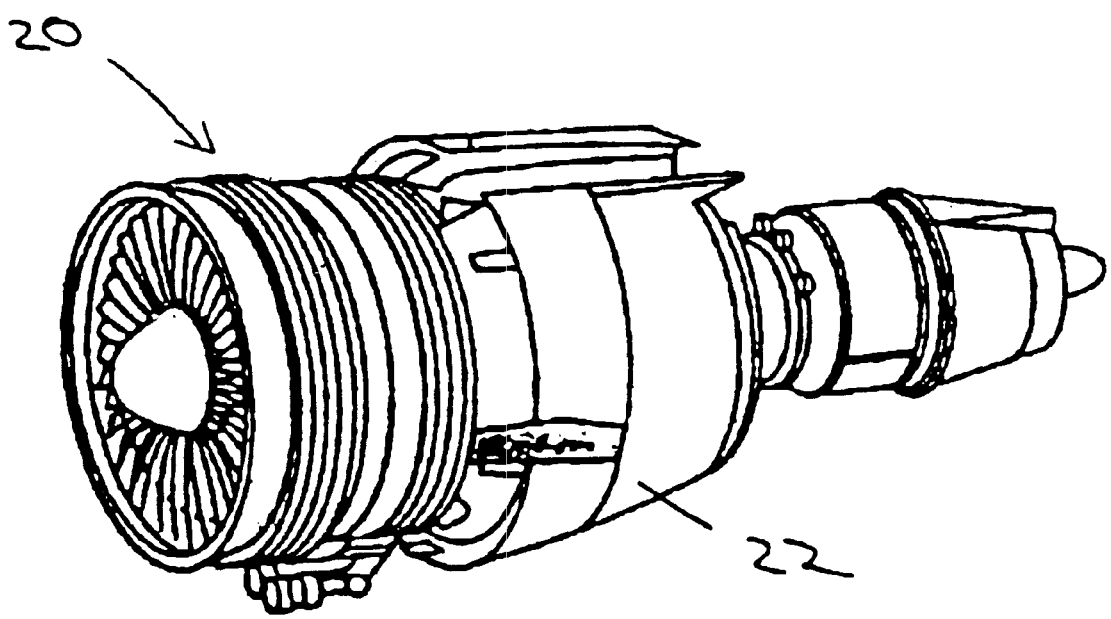
FIG. 1 is a perspective view of an aircraft gas turbine engine.
Figure 2:
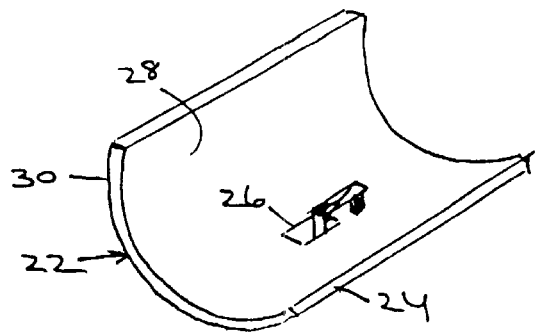
FIG. 2 is a fragmented interior view of a portion of the outer bypass duct of the engine of FIG. 1.

FIGS. 1–2 illustrate a preferred application of the present invention, although the invention is not limited to this application. An aircraft gas turbine engine 20 is a propulsive component of an aircraft. An outer bypass duct 22 is a generally hollow tubular component which conveys a flow of cooling air around hot portions of the engine. As may be seen in FIG. 2, the outer bypass duct 22 is a relatively thin-walled structure having a wall 24. The wall 24 is desirably made of a plurality of plies of a fiber-reinforced composite material that are bonded together. An access opening or path 26 extends between an interior surface 28 and an exterior surface 30 of the wall 24 of the outer bypass duct 22.

Figure 3:
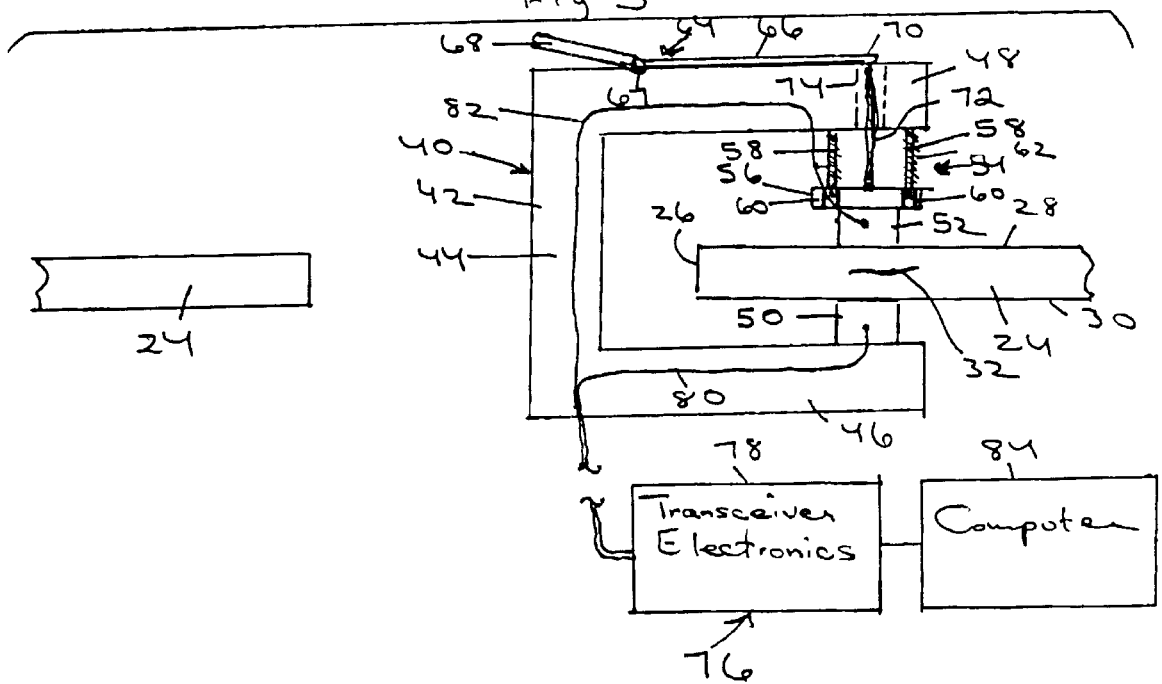
FIG. 3 is an enlarged schematic sectional view taken along line 3—3 of FIG. 2, illustrating the wall of the outer bypass duct and the ultrasonic inspection apparatus in place for performing ultrasonic testing.

FIG. 3 illustrates a hand-held ultrasonic inspection apparatus 40 that is used to search for flaws 32, such as delaminations and/or porosity, in the wall 24. The ultrasonic inspection apparatus 40 includes a yoke 42 having a base 44, a first arm 46 extending from one end of the base 44, and a second arm 48 extending from the other end of the base 44 parallel to the first arm 46. The base 44 and the arms 46 and 48 may be as long as necessary to allow the yoke to be positioned relative to the wall 24. In a prototype build by the inventors, the arms 46 and 48 are about 5 inches long, and the base 44 is about 4 inches long. The arms and base may be made shorter or longer to accommodate particular testing situations.

A first ultrasonic transducer 50 is affixed to the first arm 46. A second ultrasonic transducer 52 is in facing relation to the first ultrasonic transducer 50. A spring mount 54 attaches the second ultrasonic transducer 52 to the second arm 48 so that the second ultrasonic transducer 52 is in facing relationship to the first ultrasonic transducer 50. The spring mount 54 includes a support 56 to which the second ultrasonic transducer 52 is directly attached. Two guide rods 58 extend from the second arm 48 and engage corresponding bores 60 in the support 56. A coil spring 62 overlies each of the guide rods 58. The coil springs 62 react between the support 56 and the second arm 48, so that the support 56 and the second ultrasonic transducer 52 are biased away from the second arm 48 and toward the first ultrasonic transducer 50 with a spring bias.

A retractor 64 is affixed to the spring mount 54, and specifically to the support 56. The retractor 64 is preferably a manual retractor in the form of a lever arm 66 pivotably attached to the second arm 48 at a pivot point 67. A first end 68 of the lever arm 66 is accessible to the hand of the operator of the ultrasonic inspection apparatus 40 so that the operator may depress the first end 68. A second end 70 of the lever arm 66 is affixed to one end of a cable 72 whose other end is affixed to the support 56. The cable 72 extends through a bore 74 in the second arm 48. When the operator does not depress the first end 68, the second ultrasonic transducer 52 rests at its furthest distance from the second arm 48 under the biasing force of the coil springs 62. When the operator depresses the first end 68, the cable 72 retracts the second ultrasonic transducer 52 away from the first ultrasonic transducer 50 against the spring bias of the coil springs 62. The guide rods 58 ensure that the second ultrasonic transducer 52 maintains its facing relation to the first ultrasonic transducer 50 regardless of its state of extension or retraction.

An electronics system 76, including at least a transceiver electronics 78, is in communication with the first ultrasonic transducer 50 and the second ultrasonic transducer 52 through respective electrical leads 80 and 82. The leads 80 and 82 pass along the external surfaces of the yoke 42, as illustrated, or they may pass through interior bores provided for that purpose. The electronics system 76, and specifically the transceiver electronics 78, transmits a driver signal to one of the ultrasonic transducers 50 or 52, and receives a received signal from the other of the ultrasonic transducers 52 or 50. Ultrasonic transducers typically may be used either to send or receive a signal. The electronics system 76 may further include a computer 84 in electrical communication with the transceiver electronics 78 to analyze the signals transmitted through the wall 24 for the presence of flaws. Electronics system 76 and associated ultrasonic transducers 50, 52 are known for use in other applications.

FIG. 4 illustrates the use of the ultrasonic inspection apparatus 40. The hollow structure with the access opening is furnished, numeral 90. The ultrasonic inspection apparatus, preferably the previously discussed apparatus 40, is furnished, numeral 92. The ultrasonic inspection apparatus 40 is positioned, numeral 94, relative to the outer bypass duct 22, the access opening 26, and the wall 24. The positioning step 94 is accomplished by placing one of the arms, here the second arm 48, adjacent to the interior surface 28, the other of the arms, here the first arm 46, adjacent to the exterior surface 30, and the base 44 extending through the access opening 26, numeral 96. In cooperation with this placing step 96, the retractor 64 is operated as necessary, numeral 98, to retract the second ultrasonic transducer 52 so that the two ultrasonic transducers 50, 52 may be moved laterally across the exterior surface 30 and the interior surface 28, respectively. When the proper positioning is reached, the retractor 64 is released, numeral 100, so that the two ultrasonic transducers 50 52 are in a facing relation to each other with the wall 24, formed of the piece of composite material, captured therebetween. A thin layer of a coupling medium or couplant is usually placed between each of the transducers and the portion of the wall 24 that it contacts, to aid in the coupling of the ultrasonic signal between the ultrasonic transducer and the wall. The coupling medium may be, for example, water, oil, or a gel. Using the electronics system 76, the ultrasonic transducers 50, 52 are operated to send an ultrasonic signal from one of the ultrasonic transducers 50, 52 to the other of the ultrasonic transducers 52, 50. The ultrasonic signal passes through the thickness of the wall 24, so that the received signal may be analyzed for the presence of flaws 32 in the wall 24.

The procedure of FIG. 4 may be used to detect and track the development of flaws which are initially too small to require immediate repair or replacement of the part. For example, pores may develop at and near the interior surface 28 of the outer bypass duct 22, as a result of the heat to which it is exposed. The pores may initially be very small and of little immediate concern, and difficult to quantify. The part may be periodically tested after increasing numbers of engine cycles to determine the increase in severity of the pore flaws, until such time as it is judged that the flaws have become so severe that the part requires repair or replacement. Thus, over time and numbers of engine cycles, because of the increasing number and severity of the flaws, transmission of the ultrasonic signal at a specific location may fall from 100 percent, to 90 percent, and so on until it reaches a level that is judged to be unacceptably low. This ability to track the incidence and progression of the flaws with a convenient, hand-held instrument, is an important feature of the present invention. The tracking of the flaws is not economically feasible using the prior approach wherein the part had to be disassembled from the engine and bench tested for each inspection.

The present invention has been reduced to practice and tested using outer bypass ducts of a General Electric F404 gas turbine engine. It was also tested in laboratory surroundings to compare the results obtained using the present approach with results obtained in conventional water-tank ultrasonic testing. The results were comparable, indicating that the present approach may be used with confidence to detect flaws in field testing.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method for inspecting a structure, comprising the steps of
   furnishing a hollow structure having a wall comprising a piece of composite material, the wall having
      an interior surface,
      an exterior surface, and
      an access opening therethrough extending between the interior surface and the exterior surface;
   furnishing an ultrasonic inspection apparatus comprising
      a yoke having a base, a first arm extending from the base, and a second arm extending from the base parallel to the first arm,
      a first ultrasonic transducer affixed to the first arm,
      a second ultrasonic transducer in facing relation to the first ultrasonic transducer,
      a spring mount attaching the second ultrasonic transducer to the second arm, the spring mount comprising a spring biasing the second ultrasonic transducer toward the first ultrasonic transducer with a spring bias, and
      a retractor affixed to the spring mount to permit the second ultrasonic transducer to be retracted away from the first ultrasonic transducer against the spring bias;
   positioning the ultrasonic inspection apparatus by the steps of
      placing one of the arms adjacent to the interior surface, one of the arms adjacent to the exterior surface, and the base extending through the access opening, and
      operating the retractor to retract the second ultrasonic transducer so that the two ultrasonic transducers may be moved laterally across the interior surface and the exterior surface, and
      releasing the retractor so that the two ultrasonic transducers are in a facing relation to each other with the piece of composite material captured therebetween; and
   ultrasonically inspecting the structure, the step of ultrasonically inspecting including the step of operating the ultrasonic transducers to send an ultrasonic signal from either one of the ultrasonic transducers to the other of the ultrasonic transducers.

2. The method of claim 1, wherein the hollow structure comprises a component of an aircraft.

3. The method of claim 1, wherein the hollow structure comprises a component of a gas turbine engine.

4. The method of claim 1, wherein the hollow structure comprises an outer bypass duct of a gas turbine engine.

5. The method of claim 4, wherein the access comprises an access port in the outer bypass duct.

6. The method of claim 1, wherein the ultrasonic inspection apparatus further includes
   an electronics system in electrical communication with the first ultrasonic transducer and the second ultrasonic transducer, the electronics system transmitting a driver signal to one of the ultrasonic transducers and receiving a received signal from the other of the ultrasonic transducers.

7. The method of claim 1, wherein the retractor comprises a manually operated lever.

8. A method for inspecting a structure, comprising the steps of
   furnishing a structure having
      an interior surface,
      an exterior surface, and
      an access path extending between the interior surface and the exterior surface;
   furnishing an ultrasonic inspection apparatus comprising
      a yoke having a base, a first arm extending from the base, and a second arm extending from the base parallel to the first arm,
      a first ultrasonic transducer affixed to the first arm,
      a second ultrasonic transducer in facing relation to the first ultrasonic transducer,
      a spring mount attaching the second ultrasonic transducer to the second arm, the spring mount comprising a spring biasing the second ultrasonic transducer toward the first ultrasonic transducer with a spring bias, and
      a retractor affixed to the spring mount so as to permit the second ultrasonic transducer to be retracted away from the first ultrasonic transducer against the spring bias;
   positioning the ultrasonic inspection apparatus by the steps of
      placing one of the arms adjacent to the interior surface, one of the arms adjacent to the exterior surface, and the base extending through the access opening, and
      operating the retractor to retract the second ultrasonic transducer so that the two ultrasonic transducers may be moved laterally across the interior surface and the exterior surface, and releasing the retractor so that the two ultrasonic transducers are in a facing relation to each other with the piece of composite material captured therebetween; and ultrasonically inspecting the structure, the step of ultrasonically inspecting including the step of operating the ultrasonic transducers to send an ultrasonic signal from either one of the ultrasonic transducers to the other of the ultrasonic transducers.

9. An ultrasonic inspection apparatus comprising a yoke having a base, a first arm extending from the base, and a second arm extending from the base parallel to the first arm;

a first ultrasonic transducer affixed to the first arm;

a second ultrasonic transducer in facing relation to the first ultrasonic transducer;

a spring mount attaching the second ultrasonic transducer to the second arm, the spring mount comprising a spring biasing the second ultrasonic transducer toward the first ultrasonic transducer with a spring bias; and a retractor affixed to the spring mount so as to permit the second ultrasonic transducer to be retracted away from the first ultrasonic transducer against the spring bias.

10. The apparatus of claim 9, further including an electronics system in electrical communication with the first ultrasonic transducer and the second ultrasonic transducer, the electronics system transmitting a driver signal to one of the ultrasonic transducers and receiving a received signal from the other of the ultrasonic transducers.

11. The apparatus of claim 9, wherein the retractor comprises a manually operated lever.

12. The method of claim 1, wherein the step of inspecting includes the step of analyzing a received ultrasonic signal received by the other of the ultrasonic transducers for the presence of flaws in the structure.

13. The method of claim 1, wherein the step of positioning the ultrasonic inspection apparatus includes the step of placing a coupling medium between at least one of the ultrasonic transducers and the piece of composite material.

14. The method of claim 8, wherein the step of inspecting includes the step of analyzing a received ultrasonic signal received by the other of the ultrasonic transducers for the presence of flaws in the structure.

15. The method of claim 8, wherein the step of positioning the ultrasonic inspection apparatus includes the step of placing a coupling medium between at least one of the ultrasonic transducers and the piece of composite material.

* * * * *